United States Patent [19]

Force et al.

[11] Patent Number: 4,740,367

[45] Date of Patent: Apr. 26, 1988

[54] VEGETABLE OIL ADDUCTS AS EMOLLIENTS IN SKIN AND HAIR CARE PRODUCTS

[75] Inventors: Carlton G. Force, Mt. Pleasant; Fredricke S. Starr, Johns Island, both of S.C.

[73] Assignee: Westvaco Corporation, New York, N.Y.

[21] Appl. No.: 877,464

[22] Filed: Jun. 23, 1986

Related U.S. Application Data

[63] Continuation-in-part of Ser. No. 632,589, Jul. 19, 1984, abandoned.

[51] Int. Cl.$^4$ ............................ A61K 7/06; A61K 7/48
[52] U.S. Cl. ......................................... 424/47; 424/70; 514/846; 514/847; 514/938
[58] Field of Search ...................... 514/844; 424/47, 70

[56] References Cited

U.S. PATENT DOCUMENTS

| 2,678,934 | 5/1954 | Grummitt | 260/404.8 |
|---|---|---|---|
| 4,196,134 | 4/1980 | Ball et al. | 260/404.8 |
| 4,376,789 | 3/1983 | Lowicki et al. | 514/777 |

FOREIGN PATENT DOCUMENTS

| 4722594 | 8/1968 | Japan | 424/70 |
|---|---|---|---|
| 5531037 | 8/1978 | Japan | 424/70 |
| 57-179109 | 4/1981 | Japan | 424/70 |
| 312568 | 5/1929 | United Kingdom | 424/70 |

*Primary Examiner*—Dale R. Ore
*Attorney, Agent, or Firm*—Terry B. McDaniel; Richard L. Schmalz

[57] ABSTRACT

Certain vegetable oil lipid adducts, either alone or in combination with disproportionated vegetable oils, are disclosed which provide persistent softening effects upon incorporation in skin and hair care preparations. The emollients of the invention include both the water-soluble and water-insoluble salts of the vegetable oil adducts. The certain vegetable oil adducts of the invention are the adducts prepared from vegetable oils containing nonconjugated polyunsaturated fatty acid esters which are conjugated and then modified via Diels-Alder addition with acrylic acid, fumaric acid, or maleic anhydride.

27 Claims, 2 Drawing Sheets

STRATUM CORNEUM X-RAY DIFFRACTION

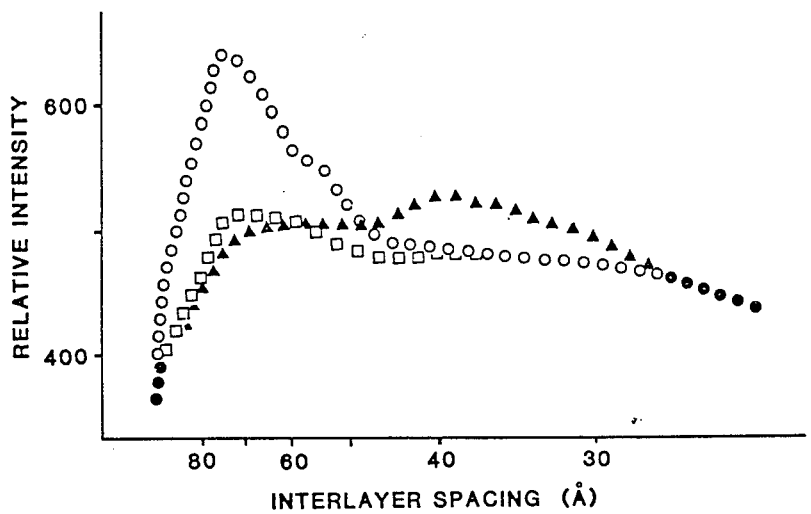

Figure 1. Effect of the oil adduct on x-ray diffraction spectrum of washed skin. ○, untreated normal stratum corneum; □, washed normal stratum corneum; ▲, washed normal stratum corneum treated with the oil adduct for one hour; ●, region of complete spectral overlap.

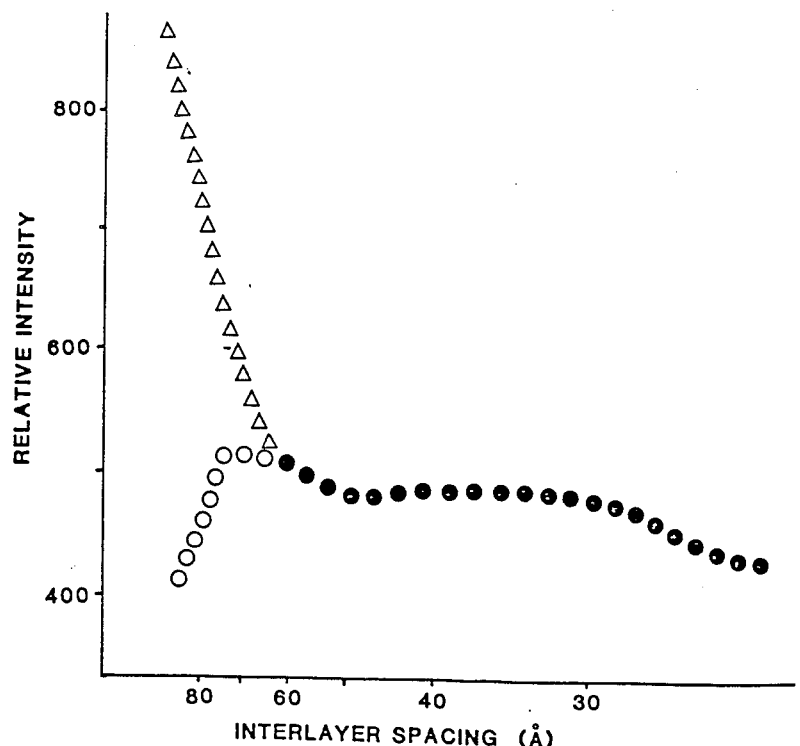

Figure 2. Comparison of x-ray diffraction spectra of washed and ether-extracted skin. △, normal stratum corneum extracted for 30 minutes with ether; ○, washed normal stratum corneum; ●, region of complete spectral overlap.

STRATUM CORNEUM X-RAY DIFFRACTION

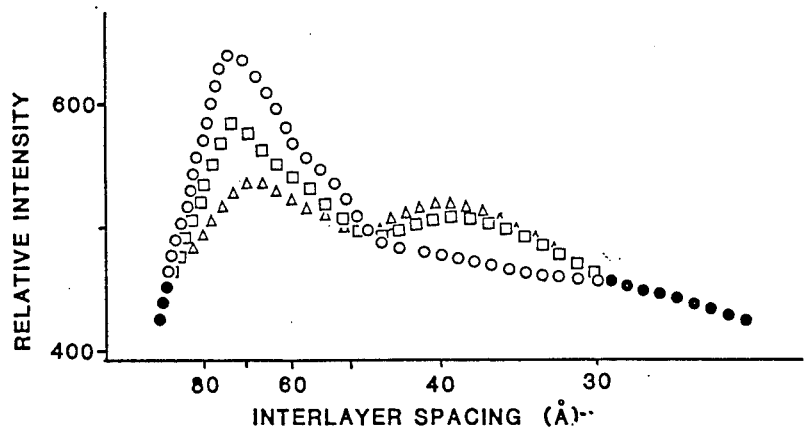

Figure 3. Effect of the oil adduct with time on x-ray diffraction spectrum of skin. ○, untreated normal stratum corneum; ☐, normal stratum corneum treated with the oil adduct for one hour; △, normal stratum corneum treated with the oil adduct for 13 hours ●, regions of complete spectral overlap.

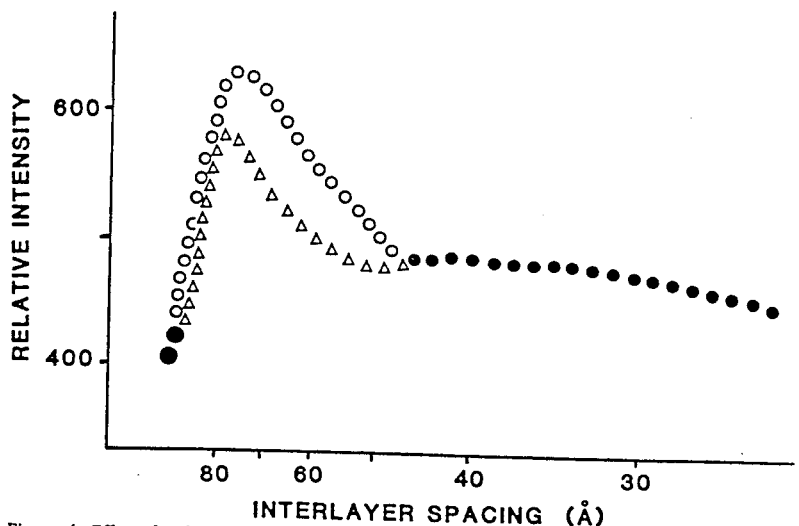

Figure 4. Effect of soybean oil on x-ray diffraction spectrum of skin. ○, normal stratum corneum; △, normal stratum corneum treated for one hour with soybean oil; ●, region of complete spectral overlap.

VEGETABLE OIL ADDUCTS AS EMOLLIENTS IN SKIN AND HAIR CARE PRODUCTS

This application is a continuation-in-part of application Ser. No. 632,589, filed July 19, 1984, titled as above, now abandoned.

BACKGROUND OF THE INVENTION (1) Field of the Invention

This invention relates to the use of vegetable oil adducts, either alone or in combination with vegetable oils and/or modified vegetable oils as additives in skin and hair care products. More particularly, this invention relates to the use of both water-soluble and water-insoluble salts of vegetable oil adducts with or without vegetable oils or modified vegetable oils as emollients in skin and hair care products. Specifically, this invention relates to the use of adducts prepared from vegetable oils containing nonconjugated polyunsaturated fatty acid esters which are conjugated and then modified via Diels-Alder addition with acrylic acid, fumaric acid or maleic anhydride as emollients in skin and hair care products.

(2) Description of the Prior Art

Skin is made up of several layers of cells which coat and protect the keratin and collagen fibrous proteins that form the skeleton of its structure. The outermost of these layers, known as the stratum corneum, is known to be composed of 250 Å protein bundles surrounded by 80 Å thick lipid layers. Anionic surfactants typically penetrate the stratum corneum membrane and, by delipidization (i.e., removal of the lipids from the stratum corneum), destroy its integrity. This destruction of the skin surface topography leads to a rough feel and may eventually permit the surfactant to interact with the keratin, creating irritation.

Organic solvents are a major cause of delipidization of the stratum corneum. Also, solvents or solvent mixtures which are both lipid soluble and water soluble are most effective in delipidization, sometimes removing as much as 10% to 20% of lipids from the skin upon long soaking. Specific chain length ranges of less water soluble organics are also deleterious. Hydrocarbons of the chain lengths present in kerosene (boiling range 272° C. to 333° C.) interact with the lipids to produce abnormal thickening of the stratum corneum. Kerosene, of course, is a common component utilized in waterless hand cleaners. Medium chain length surfactants such as sodium lauryl sulfate and $\alpha$-olefin sulfonates commonly used in dish washing detergents are deleterious to the skin even in very dilute solutions. The activity of this class of substances is thought to be due to a strong binding of the surfactant functional group with protein molecules in the keratin filaments causing them to be reversibly denatured from the $\alpha$-helix to the $\beta$-configuration through an uncoiling of the filaments which expands the tissue. Once this has occurred, complete recovery of the barrier function probably does not occur even after all of the surfactant is removed because of the complex composition and nature of the stratum corneum.

Cosmetic creams which employ mineral oil also include vegetable oils for partial replacement of skin surface lipids removed due to the solvent action of the mineral oil. However, only relatively recently has it been recognized that the moisture content of the skin is equally important.

The proper water gradient across the stratum corneum is important to its functionality. Most of this water, which is sometimes considered to be the stratum corneum's plasticizer, comes from inside the body. If the humidity is too low, such as in a cold climate, insufficient water remains in the outer layers of the stratum corneum to properly plasticize the tissue; and the skin begins to scale and becomes itchy. Skin permeability is also decreased somewhat when there is inadequate water across the stratum corneum. On the other hand, too much water on the outside of the skin causes the stratum corneum to ultimately sorb three to five times its own weight of bound water. This swells and puckers the skin and results in approximately a two to three fold increase of the permeability to water and other polar molecules above the permeability at optimum hydration.

Hair consists of many of the same constituents as the stratum corneum. The outermost region of cells forms a rather thick chemically resistant protective coating enclosing the hair fiber which is called the cuticle. The surface of the cuticle is covered with a thin layer called the epicuticle which is thought to contain lipids and protein. The cuticle envelopes the cortex cells which comprise the major part of the fiber mass. Keratinization takes place in the cortex to build stability into the hair structure.

Thus, a need exists for substances which will assist the stratum corneum and hair cuticle in maintaining their barrier and water retention functions at optimum performance in spite of deleterious interactions which the skin and hair may encounter in washing, work, and recreation.

In the discussion on cosmetic creams and lotions in the *Encyclopedia of Chemical Technology,* Third Edition, Volume 7, a classic example of a cream formulation is given which includes 11.8–12.1% spermaceti. It is also noted that modern formulations which employ mineral oil in place of the earlier used almond oil must include vegetable oil for partial replacement of skin surface lipids removed by the solvent action of the mineral oil.

Cosmetic lotion formulations are almost identical to the creams except an oil-in-water emollient lotion usually contains more water than the corresponding cream. These lotions are preferred for use during the day because they produce a lighter or less oily emollient film. Cosmetic lotion formulations in the *Encyclopedia of Chemical Technology* include 1–1.5% lanolin anhydrous as the primary emollient.

Unfortunately, emollient additives presently employed in creams and lotions do not provide the persistency desired in their skin softening effects. Therefore, a particular need exists for emollient additives which promote skin softening for a longer period of time than presently available emollients.

Hair preparations also may benefit from inclusion of emollients. The barrier and water retention functions of the hair cuticle may be assisted similarly to the stratum corneum of the skin, particularly in shampoos and hair straighteners. Lanolin and its derivatives are included in shampoo formulations as conditioning agents to impart ease of combing, detangling, body, shine, manageability, split-end mending, and prevention of static build-up.

The beneficial effects of emolliency to both skin and hair may be appreciated most in dandruff shampoos. Dandruff is the product of hyperkeratinization. The rate of keratinization increases to the point that the scales become more visible. Dandruff shampoos contain ingredients that effectively control dandruff by allowing a normal turnover rate of epidermal cells. A skin and hair softening emollient should reduce the rate of keratinization in the scalp stratum corneum and, at the same time, benefit the hair cuticle.

Therefore, an object of the present invention is to provide additives for skin and hair preparations. A further object is to provide skin and hair preparation emollient additives which give a softening effect to the skin stratum corneum or the hair cuticle. A still further object of this invention is to provide skin and hair preparation additives which provide a more persistent softening effect than known emollients.

SUMMARY OF THE INVENTION

The above stated objects are achieved in the discovery that certain vegetable oil lipid adducts, either alone or in combination with vegetable oils and/or modified vegetable oils, provide persistent softening effects upon incorporation in skin and hair care preparations. The emollients of this invention include both the water-soluble and water-insoluble salts of the vegetable oil adducts. The certain vegetable oil adducts of the invention are the adducts prepared from vegetable oils containing nonconjugated polyunsaturated fatty acid esters which are conjugated and then modified via Diels-Alder addition with acrylic acid, fumaric acid, or maleic anhydride.

DESCRIPTION OF THE PREFERRED EMBODIMENTS

The vegetable oil adducts essential to this invention may be made from vegetable oils having polyunsaturated fatty acid ester groups in the triglyceride molecule thereby increasing the carboxyl content of the fatty acid ester groups. These vegetable oil adducts are made by first conjugating and elaidinizing the nonconjugated portion of the polyunsaturated fatty acid, mainly linoleic acid, followed by Diels-Alder addition with fumaric acid, maleic anhydride or acrylic acid. It is essential that the conjugation and elaidinization take place before the acrylic addition to produce the acrylic acid adduct in optimum yield. With fumaric acid or maleic anhydride the acid or anhydride can be present at the time conjugation and elaidinization takes place without adversely affecting the reaction.

These vegetable oil adducts and their preparation are taught in U.S. Pat. No. 2,678,934 to Grummitt and U.S. Pat. No. 4,196,134 to Ball et al., the teachings of which are incorporated herein by reference. The vegetable oil adducts form triglyceride acids of the general formula

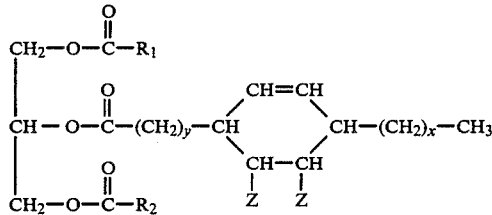

wherein x and y are integers from 3 to 9, x and y together equal 12, each Z can be a carboxylic acid group in which all or part of the carboxyl groups may be in the anhydride form or one Z can be hydrogen and the other Z a carboxylic acid group, and $R_1$ and $R_2$ are saturated-/unsaturated hydrocarbon radicals. These triglyceride acids may be converted into their soap forms including the soluble alkali metal soaps and amine soaps, the insoluble alkaline earth and higher valent metal soaps, or be incorporated as the free acid to achieve the benefits of this invention.

In U.S. Pat. No. 4,376,789, the patentees disclose reaction products of polyhydric alcohols and maleinized unsaturated fatty acids of carbon chain length $C_{10-25}$ to be useful as surfactants in skin-care products. The compounds of the present invention, however, result from maleinizing or fumarizing preformed esters. Therefore, the invention compounds are entirely dissimilar to those disclosed by the patentees.

The benefits provided by the vegetable oil adducts disclosed herein include a softening or emolliency of the skin or hair which is retained at maximum activity for a period of up to twenty hours. This activity is not diminished by normal cleaning procedures such as washing with soap and water or even cleaning with so called waterless hand cleaners consisting of a cream composed of soap, water, odorless kerosene and a variety of lesser ingredients such as lanolin and sometimes pumice stone to enhance their cosmetic and cleaning properties.

Although the discovered compounds produce good softening and moisturizing of the skin alone, it has been found that these benefits also can be achieved by blending the vegetable oil adducts with the parent oil. Moreover, these benefits can be enhanced by the addition of the parent oil if the parent oil has been disproportionated to conjugate the double bonds in the linoleic and linolenic acid groups present in the oil. Although any of the adducts mentioned are effective emollients, the adduct providing optimum effectiveness is the fumaric acid Diels-Alder product. A preferred method of achieving the optimized product is to react two moles of vegetable oil with one mole of the dienophile in the presence of catalytic amounts of iodine, the conjugation and elaidinization agent. This simultaneously produces a 50:50 blend of adduct to disproportionated vegetable oil. The 50:50 blend of the soybean oil-fumaric acid adduct and disproportionated soybean oil is referred to herein as PCW-178.

From the following examples, it can be seen that the adducts of this invention are uniquely advantageous because of the long time period over which they provide softening and emolliency to the skin. In order to remain effective for such long periods, it would appear that they must possess an affinity for or at least optimum compatibility with one or more components of the skin probably present in the stratum corneum. This could be an interaction of the hydrophobic portions of the adduct and free vegetable oil, if it is present, with lipid granules in the intercellular space or the more hydrophilic lipids which make up the walls of the keratinized cells. If the adduct were capable of entering the cell, its carboxylic acid groups might interact with protein amine groups around the exterior of α-helical disulfide bonded keratin chains. Regardless of how it is retained within the skin, the soybean oil fumaric acid adduct has been demonstrated to possess a very large hydrophilic group area of about 97.5 Å$^2$ for the free acid and 116.2 Å$^2$ for the disodium soap. By comparison, the head group of monocarboxylic fatty acids only occupies 35 Å$^2$. It would be anticipated that this large a polar region might hydrogen bond considerable amounts of water. Thus, it could effectively moisturize the skin with water in the regions where it is located. Although the exact mechanism by which these adducts function is unknown, their effectiveness is surprising.

EXAMPLE 1

In the one step preparation of an optimized blend of 50% soybean oil fumaric acid adduct and 50% conjugated soybean oil, 164 lbs (0.188 lb/moles) of food grade refined soybean oil, 10.6 lbs (0.091 lb/moles) fumaric acid and 0.66 lb iodine were added to a 30-gallon pressure reaction vessel. The reactor was sealed, heated to 250° C. and held at this temperature for four hours while the contents were being stirred. The resulting product had an acid number of 63.6 and a color of 3+ on the Gardner scale.

EXAMPLE 2

The preparation of the soybean oil fumaric acid adduct was performed by adding 200 lbs of refined soybean oil, 26 lbs of fumaric acid and 0.60 lb of iodine to a 30-gallon pressure reactor. The reactor was sealed, heated to 210° C. and held at that temperature for four hours with stirring. The resulting product had an acid number of 114.8 and a color of 5 on the Gardner scale.

EXAMPLE 3

This example illustrates the preparation of alkali metal soaps and their efficacy in skin care.

To a 400 ml beaker equipped with a stirrer were added 113.12 grams of water and 13.12 grams of potassium hydroxide pellets (86% solids). After heating the solution to 60° C., 100 grams of soybean oil fumaric acid adduct from Example 2 was slowly added with stirring. After 15 minutes additional stirring at 60° C., the mixture was allowed to cool. The viscosity of the yellow product was 2,050 centipoise at 50° C., and its pH was 8.45.

To a 150 ml beaker containing 50 grams of the above 50% solids potassium soap of the soybean oil fumaric acid adduct, 25 grams of soybean oil was slowly added while good agitation was maintained. The resulting system had a viscosity of 7,100 centipoise and a pH of 8.3.

Application to the skin produced a smooth soft feel without slipperiness or other undesirable properties. While rubbing the skin to adsorb the last of the product, the skin developed a slightly sticky feel for an instant until all of the product had disappeared from sight. The normal routine of work, recreation and rest was carried out for the next 20 hours which included considerable exposure to water using both hand soap and liquid dishwashing detergent. At the end of the 20 hours, the skin still possessed the smooth softness which the product had originally imparted.

EXAMPLE 4

The sodium soap of the soybean oil fumaric acid adduct was prepared by heating 108 grams of water in which was dissolved 8.4 grams of sodium hydroxide pellets (97.6% solids) to 60° C. and adding 100 grams of soybean oil fumaric acid adduct from Example 2. After stirring 15 minutes at 60° C., the soap was allowed to cool. It had a pH of 8.6 and viscosity of 2,160 centipoise at 45° C.

In a 250 ml beaker, 40 grams of soybean oil was slowly added to 80 grams of the above sodium soap. This gave a system with viscosity of 3,200 centipoise and pH 8.7. There was no sticky feel at any stage during the rubbing of this product into the skin. It exhibited similar long lasting skin softening to the potassium soap.

EXAMPLE 5

To illustrate the preparation of a monovalent amine salt, an anhydrous triethanol amine soap was prepared by mixing 13.9 grams of triethanol amine into 100 grams of soybean oil fumaric acid adduct from Example 2 to give a clear viscous gel. This soap showed skin softening properties similar to the alkali metal soaps. It was compounded into soft soap formulations where it assisted in pearlescent and improved rinsing from the skin without detracting from the lathering properties of the soft soap.

EXAMPLE 6

This example illustrates the utility of soaps of multivalent metal ions and soybean oil fumaric acid adduct in skin care.

In a 500 ml beaker, 9.29 grams of sodium hydroxide pellets (97.6% solids) were dissolved in 121 ml of water. One Hundred (100) grams of soybean oil fumaric acid adduct from Example 2 was then added. After stirring 20 minutes to produce a viscous homogeneous soap, a solution consisting of 24.85 grams of magnesium sulfate heptahydrate dissolved in 71 ml of water was added over a period of 15 minutes. After about 2/3 of the magnesium sulfate solution had been added, the viscous homogeneous soap separated into a two phase system. After stirring for one hour and allowing the system to settle for another hour, the aqueous phase was poured off; and the viscous gel was washed twice with 131 ml portions of distilled water to remove any remaining sodium sulfate. Each batch of wash water was stirred with the organic phase for an hour; then the system was allowed to settle for another hour before removing from the organic phase. Handling of this magnesium soap of soybean oil fumaric acid adduct produced a smooth soft feel to the hands which remained for days after application.

EXAMPLE 7

This example illustrates the ability of soybean oil fumaric acid adduct and conjugated soybean oil to provide skin softness and overcome the deleterious effects of kerosene on the skin.

A viscous but pourable soap of the soybean oil fumaric acid adduct-conjugated soybean oil blend in Example 1 was prepared by slowly adding 50 grams of the adduct to a solution of 56.56 grams of potassium hydroxide pellets (86% solids) dissolved in 56.56 grams of water. The turbid solution had a pH of about 8.5.

To 17 grams of the above soap in a 35 ml screw cap bottle was added kerosene in 3 ml increments until the bottle was full. After each incremental addition of kerosene, the system was stirred with a magnetic stirrer for 45 minutes. The final solution was low in viscosity and clear. This blend was found to clean hidden dirt from the fingerprint pattern and other crevices of the hands as evidenced by black colored deposit on a dry paper towel used to wipe it off and the visually improved cleanliness of the skin. Further, its viscosity was sufficiently low for it to be easily worked under the fingernails to remove grease and grime, a particularly difficult task for mechanics.

In contrast to commercially available waterless hand cleaners typically composed of about 40% kerosene, 40% water and 20% oleic acid type soap, the formulation of this example provided skin softening similar to that of hand creams which lasted for several hours. There was also no tendency for this formulation to produce painful cracks deep into the stratum corneum in the fingerprint areas of the hands which is the common fault of the commercial waterless hand cleaners.

EXAMPLE 8

The product of Example 1 (designated as PCW-178) was directly compared to anhydrous lanolin and the refined, less viscous lanolin oil for emollient properties in a typical hand lotion formulation at a level of 5%. The evaluation procedure employed was that developed by Goldemberg and De la Rosa described in their article "Correlation of Skin Feel of Emollients to Their Chemical Structure," *J. Soc. Cosmet. Chem.* 22:635–654 (1971). The emulsions in each case were evaluated as unmarked samples by the same panel of laboratory workers for comparisons of initial feel on the skin, behavior during rub-in, and final feel after the emulsion had been absorbed into the skin. Initial Slip was rated on a scale from 1 to 5 (slight to much slip). End Feel was rated for smoothness, oiliness, friction and moistness. Each of these four qualities was rated on a scale of 1 to 5, with 5 representing the most desirable feel. A numerical value for End Feel was obtained by adding together the scores for each quality rated. Possible values for End Feel thus ranged from 4 to 20. The results are presented in the table presented below.

TABLE I

"APPLICATION" PROPERTIES OF LOTION

| Emollient | Initial Slip | End Feel | | | |
|---|---|---|---|---|---|
| | | Smoothness | Oiliness | Friction | Moistness |
| Anhydrous Lanolin | 4 | 3 | 3 | 1 | 3 |
| | 1 | 2 | 1 | 2 | 3 |
| | 3 | 5 | 4 | 4 | 5 |
| | 3 | 3 | 3 | 1 | 3 |
| | 5 | 4 | 4 | 5 | 4 |
| | 16 | 17 | 13 | 13 | 18 |
| | Average Score 3.2 | | Total - 61 Average Score 12.2 | | |
| Lanolin Oil | 3 | 3 | 2 | 1 | 2 |
| | 2 | 3 | 1 | 3 | 3 |
| | 5 | 5 | 4 | 3 | 5 |
| | 3 | 3 | 4 | 2 | 2 |
| | 5 | 5 | 4 | 5 | 4 |
| | 18 | 19 | 15 | 14 | 16 |
| | Average Score 3.6 | | Total - 64 Average Score 12.8 | | |
| PCW-178 | 2 | 3 | 3 | 4 | 4 |
| | 2 | 3 | 1 | 3 | 4 |
| | 1 | 5 | 5 | 5 | 5 |
| | 4 | 4 | 4 | 2 | 3 |
| | 4 | 4 | 5 | 4 | 4 |
| | 13 | 19 | 18 | 18 | 20 |
| | Average Score 2.6 | | Total - 75 Average Score 15.0 | | |

Although the Initial Slip was not rated as favorably, the emollient of the invention was rated superior to both commercial emollients in End Feel.

EXAMPLE 9

Based on the results of phase behavior studies of the interaction between the invention vegetable oil adduct and a model skin surface lipid, it is suspected that the adduct's ability to soften the skin may be linked to its interactions with the lipids of the skin. The apparent conclusion is that the adduct's skin softening properties, unlike other skin softeners which affect either the proteins or moisture content of the skin, are due to effects upon the lipids of the skin.

In order to clarify this point, a study of human thin skin stratum corneum was made separately using small angle x-ray diffraction. Fresh full thickness samples of human skin were obtained from radical mastectomy cases and prepared by a method described by Lampe et al., *Journal of Lipids Research*, v. 24, 131–140 (1983). The skin samples were from normal skin well away from the tumor site.

The samples, taken from the same skin specimen, were then prepared for low-angle x-ray measurements by one or more of the following techniques. "Washed" samples were vortexed in a 0.1% (by weight) Ivory ® soap solution for ten minutes. Samples "treated with adduct" were spread on filter paper soaked with purified soybean oil-fumaric acid adduct and allowed to remain in contact with the oil adduct for one to thirteen hours. "Extracted" samples were vortexed in ethyl ether for 30 minutes. The prepared stratum corneum sheets were then rolled and placed in a 0.7-mm glass capillary tube and examined by small-angle x-ray diffraction. The untreated stratum corneum band was checked by multiple measurements of skin specimens from three different subjects, while the treated, washed, and extracted samples were determined by duplicate measurements from the same skin specimen. Only slight differences in intensity were encountered between spectra of the multiple runs. All glassware was thoroughly cleaned and ultimately rinsed with ether to eliminate the possibility of external lipid contamination.

Small-angle x-ray diffraction spectra were collected for seven hours using a Kiessig low-angle camera. Ni-filtered Cu radiation was used and the reflections determined by a Tennelec position-sensitive detection system (Model PSD-1100).

As can be seen in FIG. 1, untreated normal stratum corneum lipid content gave a characteristic broad diffraction peak of moderate intensity in the range of 50–80 Å. No other bands were distinguishable over the complete available range of 20–160 Å for collection times of twelve hours. This 50–80 Å band (thus, the lipids it represented) was removed both by washing and by extraction with ether as seen in FIG. 2.

Treatment with the vegetable oil adduct produced a weak diffraction from 30–45 Å. As can be seen from FIG 3, the intensity of this diffraction increased slightly as the treatment duration increased from one hour to thirteen hours, while the intensity of the 50–80 Å band significantly decreased for the same change in treatment duration. Treatment of the stratum corneum with unmodified soybean oil for one hour produced a narrower, slightly shifted diffraction peak from 60–80 Å. This spectrum is compared to the normal stratum corneum pattern in FIG. 4. Purified vegetable oil adduct by itself (unassociated with lipids) produced no diffraction pattern.

Thus, stratum corneum treated with soybean oil (FIG. 4) showed little difference in lipid interlayer spacing, while treatment with the purified invention oil adduct caused a new band to appear at 30–45 Å. Hence, the comparison of soybean oil-treated stratum corneum with adduct-treated stratum corneum demonstrates that the 30–45 Å band is neither the result of the adduct's triglyceride structure nor trace impurities remaining in the purified vegetable oil adduct.

EXAMPLE 10

Another set of emulsion formulations includes a cream and a lotion. The formula for each is:

| Ingredient | Cream 409F % | Lotion 411F % |
|---|---|---|
| PCW-178 | 16.00 | 16.00 |
| Mineral Oil | 4.00 | 4.00 |
| Cetyl Alcohol | 4.00 | 2.00 |
| Ethoxylated Stearyl Alcohol and Stearyl Alcohol Blend | 6.00 | 4.00 |
| Glycerin | 5.00 | 5.00 |
| Methylparaben | 0.15 | 0.18 |
| Purified Water, USP | 64.85 | 68.82 |

The above formulae illustrate the skin feel, low tack and non-greasy, quality feel even though a mineral oil (petrolatum) is used. PCW-178 was found to be easily formulated into emulsion products of the types produced.

EXAMPLE 11

In addition to skin care formulations, the vegetable oil adduct has shown promise for hair management products. Formula 118F shown below is an aerosol hair conditioner which leaves a film of pure adduct on the hair. It illustrates the feasibility of using the adduct in hair sprays and confirms the lack of greasiness or hair limpness that is a side effect and compromise experienced when using quaternary surfactant based conditioners and antistatics.

| AEROSOL HAIR CONDITIONER 118F | % |
|---|---|
| Denatured Alcohol | 4.0 |
| PCW-178 | 3.0 |
| Dimethicone | 5.0 |
| Propellant A-31 (Isobutane) | 88.0 |

EXAMPLE 12

Although not economically feasible, the improved results in enhanced persistency of skin softening and enhanced softening of hair cuticle are achieved by direct application of the vegetable oil adduct to the skin and hair without other additives or vehicles. Likewise, the vegetable oil adduct may be employed in combination with the disproportionated parent vegetable oil. However, the benefits of the instant invention are economically achieved via the following formulations comprising both an oil phase component, "A," and a water phase component "B." The formulation procedure in all cases is to heat A and B separately to about 70°–80° C. With mild agitation, add A to B. Continue stirring and cool to about 40° C. Add the fragrance and water while continuing to mix until the product temperature reaches about 35° C.

| FOUNDATION LOTION | | % |
|---|---|---|
| A | PCW-178 | 5.0 |
| | Cetyl Alcohol | 5.0 |
| | Mineral Oil | 4.0 |
| | Isopropyl Myristate | 5.0 |
| | Propylparaben (as preservative) | 0.1 |
| B | Glycerin | 8.0 |
| | Triethanolamine | 3.0 |
| | Methylparaben (preservative) | 0.2 |
| | Fragrance | 0.05 |
| | Purified Water, USP | qs* |

*Water is added as required to total 100%. Since water is introduced at 40° C., some water may be lost before the formulation is cooled. How much is lost will determine how much total water is required.

| HAND LOTION | | % |
|---|---|---|
| A | PCW-178 | 8.0 |
| | Cetyl Alcohol | 2.0 |
| | Propylene Glycol | 1.0 |
| | Petrolatum | 2.0 |
| | Isopropyl Myristate | 4.0 |
| | Propylparaben | 0.1 |
| | Dimethicone | 0.5 |
| | Polyacrylate Thickener (Carbomer) | 0.2 |
| B | Triethanolamine | 3.2 |
| | Glycerin | 5.0 |
| | Methylparaben | 0.2 |
| | Fragrance | 0.05 |
| | Purified Water, USP | qs |

| MOISTURIZING CREAM | | % |
|---|---|---|
| A | PCW-178 | 12.0 |
| | Cetyl Alcohol | 2.5 |
| | Petrolatum | 3.0 |
| | Isopropyl Myristate | 1.0 |
| | Acetylated Lanolin Alcohol | 1.0 |
| | Glyceryl Monostearate (self-emulsifying) | 5.0 |
| | Propylparaben | 0.1 |
| B | Glycerin | 5.0 |
| | Methylparaben | 0.2 |
| | Triethanolamine | 2.5 |
| | Fragrance | 0.05 |
| | Purified Water, USP | qs |

| HAND AND BODY LOTION | | % |
|---|---|---|
| A | PCW-178 | 5.0 |
| | Cetyl Alcohol | 2.0 |
| | Ethoxylated Stearyl Alcohol and Stearyl Alcohol Blend | 2.0 |
| | Petrolatum | 4.0 |
| | Lanolin Oil | 0.5 |
| | Acetylated Lanolin Alcohol | 1.0 |
| | Propylene Glycol | 1.0 |
| | Propylparaben | 0.1 |
| | Polyacrylate Thickener | 0.1 |
| B | Triethanolamine | 2.0 |
| | Methylparaben | 0.2 |
| | Fragrance | 0.05 |
| | Purified Water, USP | qs |

| PROTECTIVE HAND CREAM | | % |
|---|---|---|
| A | PCW-178 | 16.0 |
| | Cetyl Alcohol | 2.5 |
| | Petrolatum | 4.0 |
| | Glyceryl Monostearate, SE | 6.0 |

PROTECTIVE HAND CREAM

| | | % |
|---|---|---|
| | Silicone Polymers | 5.0 |
| | Stearic Acid | 2.0 |
| | Propylparaben | 0.1 |
| B | Triethanolamine | 2.0 |
| | Glycerin | 5.0 |
| | Methylparaben | 0.2 |
| | Purified Water, USP | qs |

OIL IN WATER COLD CREAM

| | | % |
|---|---|---|
| A | PCW-178 | 4.0 |
| | Mineral Oil | 4.5 |
| | Petrolatum | 3.0 |
| | Stearyl Alcohol | 2.0 |
| | Lanolin Oil | 2.0 |
| | Glyceryl Monostearate and PEG 100 Stearate Blend | 15.0 |
| | Propylparaben | 0.1 |
| B | Glycerin | 2.0 |
| | Methylparaben | 0.2 |
| | Fragrance | 0.05 |
| | Purified Water, USP | qs |

LUBRICATING CREAM

| | | % |
|---|---|---|
| A | PCW-178 | 16.0 |
| | Petrolatum | 13.0 |
| | Propylene Glycol Monostearate | 4.0 |
| | Cetyl Alcohol | 2.0 |
| | Mineral Oil | 4.0 |
| | Stearic Acid | 3.0 |
| | Propylparaben | 0.1 |
| B | Methylparaben | 0.2 |
| | Triethanolamine | 3.0 |
| | Glycerin | 6.0 |
| | Fragrance | 0.05 |
| | Purified Water, USP | qs |

MOISTURIZING CREAM

| | | % |
|---|---|---|
| A | PCW-178 | 12.0 |
| | Cetyl Alcohol | 3.5 |
| | Petrolatum | 3.0 |
| | Isopropyl Myristate | 1.0 |
| | Acetylated Lanolin Alcohol | 1.0 |
| | Triethanolamine | 2.5 |
| | Glyceryl Monostearate, SE | 5.0 |
| | Propylparaben | 0.1 |
| B | Glycerin | 5.0 |
| | Methylparaben | 0.2 |
| | Disodium EDTA (Ethylenediaminetetraacetic Acid) | 0.1 |
| | Fragrance | 0.05 |
| | Purified Water, USP | qs |

CLEANSING LOTION

| | | % |
|---|---|---|
| A | PCW-178 | 2.0 |
| | Cetyl Alcohol | 2.0 |
| | Stearyl Alcohol | 0.5 |
| | Isopropyl Myristate | 1.0 |
| | Propylparaben | 0.1 |
| B | Sodium Lauryl Sulfate | 0.5 |
| | Methylparaben | 0.2 |
| | Fragrance | 0.05 |
| | Purified Water, USP | qs |

OIL IN WATER COLD CREAM

| | | % |
|---|---|---|
| A | PCW-178 | 4.0 |
| | Mineral Oil | 4.5 |
| | Petrolatum | 3.0 |
| | Stearyl Alcohol | 2.0 |
| | Cetyl Alcohol | 1.0 |
| | Lanolin Oil | 2.0 |
| | Glyceryl Monostearate | 15.0 |
| | Propylparaben | 0.1 |
| B | Glycerin | 2.0 |
| | Methylparaben | 0.2 |
| | Fragrance | 0.05 |
| | Purified Water, USP | qs |

While the invention has been described and illustrated herein by references to various specific materials, procedures and examples, it is understood that the invention is not restricted to the particular materials, combinations of materials, and procedures selected for the purpose. Numerous variations of such details can be employed, as will be appreciated by those skilled in the art.

What is claimed is:

1. An improved skin care formulation including, as an emollient therefor, vegetable oil adducts, wherein the improvement comprises enhanced persistency of softening provided by adducts prepared from vegetable oils containing non-conjugated polyunsaturated fatty acid esters which are conjugated and elaidinized and then modified via Diels-Alder addition with a member of the group consisting of acrylic acid, fumaric acid or maleic anhydride.

2. The improved skin care formulation of claim 1 wherein the vegetable oil is soybean oil.

3. The improved skin care formulation of claim 1 which also includes as an emollient a member of the group selected from a vegetable oil, a modified vegetable oil produced by disproportionating the vegetable oil to conjugate the double bonds in the linoleic and linolenic acid groups present in the oil, and a mixture thereof.

4. The improved skin care formulation of claim 1 wherein the Diels-Alder modification reaction occurs by reacting the vegetable oil with fumaric acid.

5. The improved skin care formulation of claim 1 wherein the vegetable oil adduct has the general formula

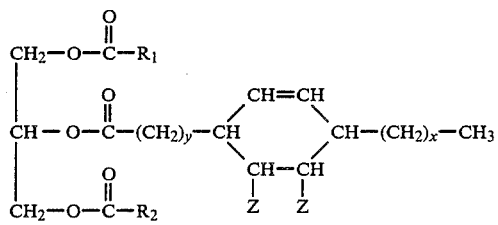

wherein x and y are integers from 3 to 9, x and y together equal 12, at least one Z is a carboxylic acid group, and any remaining Z is hydrogen, and $R_1$ and $R_2$ are saturated/unsaturated hydrocarbon radicals.

6. The improved skin care formulation of claim 5 wherein each Z is a carboxylic acid group in which all or part of the carboxyl groups may be in the anhydride form.

7. The improved skin care formulation of claim 1 wherein the vegetable oil adducts are subsequently converted into their soap forms selected from the group consisting of the soluble alkali metal and amine soaps and the insoluble alkaline earth and higher valent metal soaps.

8. The improved skin care formulation of claim 1 comprised of soybean oil-fumaric acid Diels-Alder adduct 16.00%, mineral oil 4.00%, cetyl alcohol 2.00%, ethoxylated stearyl alcohol and stearyl alcohol blend 4.00%, glycerin 5.00%, methylparaben 0.18%, and purified water, USP 68.82%.

9. The improved skin care formulation of claim 1 as follows: soybean oil-fumaric acid Diels-Alder adduct 16.00%, mineral oil 4.00%, cetyl alcohol 4.00%, ethoxylated stearyl alcohol and stearyl alcohol blend 6.00%, glycerin 5.00%, methylparaben 0.15%, and purified water, USP 64.85%.

10. The improved skin care formulation of claim 1 comprising an oil phase, "A," and a water phase, "B," as follows:

A is a soybean oil-fumaric acid Diels-Alder adduct 5.0%, cetyl alcohol is 5.0%, mineral oil is 4.0%, isopropyl myristate 5.0%, propylparaben 0.1%;

B is glycerin 8.0%, triethanolamine 3.0%, methylparaben 0.2%; and fragrance 0.05%, purified water, USP qs wherein A and B are heated separately to about 70°-80° C., A is then added to B with mild agitation and the combined materials are cooled to about 40° C. at which time the fragrance and water are added and mixing is continued until the product temperature reaches about 35° C.

11. The improved skin care formulation of claim 1 comprising an oil phase, "A," and a water phase, "B," as follows:

A is a soybean oil-fumaric acid Diels-Alder adduct 8.0%, cetyl alcohol 2.0%, propylene glycol 1.0%, petrolatum 2.0%, isopropyl myristate 4.0%, propylparaben 0.1%, dimethicone 0.5%;

polyacrylate filler 0.2%;

B is triethanolamine 3.2%, glycerin 5.0%, methylparaben 0.2%; and fragrance 0.05%, purified water, USP qs wherein A and B are heated separately to about 70°-80° C., A is then added to B with mild agitation and the combined materials are cooled to about 40° C. at which time the fragrance and water are added and mixing is continued until the product temperature reaches about 35° C.

12. The improved skin care formulation of claim 1 comprising an oil phase, "A," and a water phase, "B," as follows:

A is a soybean oil-fumaric acid Diels-Alder adduct 12.0%, cetyl alcohol 2.5%, petrolatum 3.0%, isopropyl myristate 1.0%, acetylated lanolin alcohol 1.0%, glyceryl monostearate 5.0%, propylparaben 0.1%;

B is glycerin 5.0%, methylparaben 0.2%, triethanolamine 2.5%; and fragrance 0.05%, purified water, USP qs wherein A and B are heated separately to about 70°-80° C., A is then added to B with mild agitation and the combined materials are cooled to about 40° C. at which time the fragrance and water are added and mixing is continued until the product temperature reaches about 35° C.

13. The improved skin care formulation of claim 1 comprising an oil phase, "A," and a water phase, "B," as follows:

A is a soybean oil-fumaric acid Diels-Alder adduct 5.0%, cetyl alcohol 2.0%, ethoxylated stearyl alcohol and stearyl alcohol blend 2.0%, petrolatum 4.0%, lanolin oil 0.5%, acetylated lanolin alcohol 1.0%, propylene glycol 1.0%, propylparaben 0.1%;

polyacrylate thickener 0.1%;

B is triethanolamine 2.0%, methylparaben 0.2%; and fragrance 0.05%, purified water, USP qs wherein A and B are heated separately to about 70°-80° C., A is then added to B with mild agitation and the combined materials are cooled to about 40° C. at which time the fragrance and water are added and mixing is continued until the product temperature reaches about 35° C.

14. The improved skin care formulation of claim 1 comprising an oil phase, "A," and a water phase, "B," as follows:

A is a soybean oil-fumaric acid Diels-Alder adduct 16.0%, cetyl alcohol 2.5%, petrolatum 4.0%, glyceryl monostearate 6.0%, dimethicone 5.0%, stearic acid 2.0%, propylparaben 0.1%;

B is triethanolamine 2.0%, glycerin 5.0%, methylparaben 0.2%; and purified water, USP qs wherein A and B are heated separately to about 70°-80° C., A is then added to B with mild agitation and the combined materials are cooled to about 40° C. at which time the fragrance and water are added and mixing is continued until the product temperature reaches about 35° C.

15. The improved skin care formulation of claim 1 comprising an oil phase, "A," and water phase, "B," as follows:

A is a soybean oil-fumaric acid Diels-Alder adduct 4.0%, mineral oil 4.5%, petrolatum 3.0%, stearyl alcohol 2.0%, lanolin oil 2.0%, glyceryl monostearate and PEG 100 stearate blend 15.0%, propylparaben 0.1%;

B is glycerin 2.0%, methylparaben 0.2%; and fragrance 0.05%, purified water, USP qs wherein A and B are heated separately to about 70°-80° C., A is then added to B with mild agitation and the combined materials are cooled to about 40° C. at which time the fragrance and water are added and mixing is continued until the product temperature reaches about 35° C.

16. The improved skin care formulation of claim 1 comprising an oil phase, "A," and a water phase, "B," as follows:

A is a soybean oil-fumaric acid Diels-Alder adduct 16.0%, petrolatum 13.0%, propylene glycol monostearate 4.0%, cetyl alcohol 2.0%, mineral oil 4.0%, stearic acid 3.0%, propylparaben 0.1%;

B is methylparaben 0.2%, triethanolamine 3.0%, glycerin 6.0%; and fragrance 0.05%, purified water, USP qs wherein A and B are heated separately to about 70°-80° C., A is then added to B with mild agitation and the combined materials are cooled to about 40° C. at which time the fragrance and water are added and mixing is continued until the product temperature reaches about 35° C.

17. The improved skin care formulation of claim 1 comprising an oil phase, "A," and a water phase, "B," as follows:
   A is a soybean oil-fumaric acid Diels-Alder adduct 12.0%, cetyl alcohol 3.5%, petrolatum 3.0%, isopropyl myristate 1.0%, acetylated lanolin alcohol 1.0%, triethanolamine 2.5%, glyceryl monostearate, SE 5.0%, propylparaben 0.1%;
   B is glycerin 5.0%, methylparaben 0.2%, disodium EDTA 0.1%; and
   fragrance 0.05%, purified water, USP qs
wherein A and B are heated separately to about 70°-80° C., A is then added to B with mild agitation and the combined materials are cooled to about 40° C. at which time the fragrance and water are added and mixing is continued until the product temperature reaches about 35° C.

18. The improved skin care formulation of claim 1 comprising an oil phase, "A," and a water phase, "B," as follows:
   A is a soybean oil-fumaric acid Diels-Alder adduct 2.0%, cetyl alcohol 2.0%, stearyl alcohol 0.5%, isopropyl myristate 1.0%, propylparaben 0.1%;
   B is sodium lauryl sulfate 0.5%, methylparaben 0.2%; and
   fragrance 0.05%, purified water, USP qs
wherein A and B are heated separately to about 70°-80° C., A is then added to B with mild agitation and the combined materials are cooled to about 40° C. at which time the fragrance and water are added and mixing is continued until the product temperature reaches about 35° C.

19. The improved skin care formulation of claim 1 comprising an oil phase, "A," and a water phase, "B," as follows:
   A is a soybean oil-fumaric acid Diels-Alder adduct 4.0%, mineral oil 4.5%, petrolatum 3.0%, stearyl alcohol 2.0%, cetyl alcohol 1.0%, lanolin oil 2.0%, glyceryl monostearate and PEG 100 stearate blend 15.0%, propylparaben 0.1%;
   B is glycerin 2.0%, methylparaben 0.2%; and
   fragrance 0.05%, purified water, USP qs
wherein A and B are heated separately to about 70°-80° C., A is then added to B with mild agitation and the combined materials are cooled to about 40° C. at which time the fragrance and water are added and mixing is continued until the product temperature reaches about 35° C.

20. An improved hair care preparation including as an emollient therefor, vegetable oil adducts, wherein the improvement comprises enhanced softening of hair cuticle provided by adducts prepared from vegetable oils containing non-conjugated polyunsaturated fatty acid esters which are conjugated and elaidinized and then modified via Diels-Alder addition with a member of the group consisting of acrylic acid, fumaric acid or maleic anhydride.

21. The improved hair care preparation of claim 20 wherein the vegetable oil is soybean oil.

22. The improved hair care preparation of claim 20 which also includes as an emollient a member of the group selected from a vegetable oil, a modified vegetable oil produced by disproportionating the oil to conjugate the double bonds in the linoleic and linolenic acid groups present in the oil, and a mixture thereof.

23. The improved hair care preparation of claim 20 wherein the Diels-Alder modification reaction occurs by reacting the vegetable oil with fumaric acid.

24. The improved hair care preparation of claim 20 wherein the vegetable oil adduct has the general formula

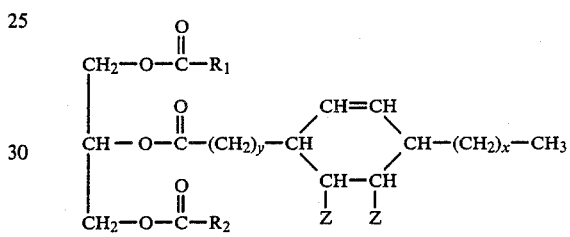

wherein x and y are integers from 3 to 9, x and y together equal 12, at least one Z is a carboxylic acid group, and any remaining Z is hydrogen, and $R_1$ and $R_2$ are saturated/unsaturated hydrocarbon radicals.

25. The improved hair care preparation of claim 20 wherein the vegetable oil adducts are subsequently converted into their soap forms selected from the group consisting of the soluble alkali metal and amine soaps and the insoluble alkaline earth and higher valent metal soaps.

26. The improved hair care preparation of claim 24 wherein each Z is a carboxylic acid group in which all or part of the carboxyl groups may be in the anhydride form.

27. The improved hair care preparation of claim 20 as follows: denatured alcohol 4.0%, a soybean oil-fumaric acid Diels-Alder adduct 3.0%, dimethicone 5.0%, and isobutane 88.0%.

* * * * *